United States Patent [19]

Burstein et al.

[11] Patent Number: 5,290,272

[45] Date of Patent: Mar. 1, 1994

[54] METHOD FOR THE JOINING OF OCULAR TISSUES USING LASER LIGHT

[75] Inventors: Neal I. Burstein, Longmont, Colo.; John M. Williams, Sr., Marshfield, Wis.; Michael J. Nowicki, Longmont; William Q. Jeffers, Boulder, both of Colo.

[73] Assignee: Helios Inc., Longmont, Colo.

[21] Appl. No.: 851,822

[22] Filed: Mar. 16, 1992

[51] Int. Cl.$^5$ .............................................. A61N 5/06
[52] U.S. Cl. ........................................... 606/4; 606/3; 606/6; 128/898
[58] Field of Search ................. 606/3, 4, 5, 6, 107; 623/5; 128/898

[56] References Cited

U.S. PATENT DOCUMENTS

| | | |
|---|---|---|
| 3,467,099 | 9/1969 | Lotmar . |
| 3,487,835 | 10/1963 | Koester et al. . |
| 3,547,125 | 12/1970 | Tagnon . |
| 3,930,504 | 1/1976 | de Laforcade . |
| 4,526,170 | 7/1985 | Tanner . |
| 4,537,193 | 8/1985 | Tanner . |
| 4,633,866 | 1/1987 | Peyman et al. .......... 606/4 |
| 4,633,870 | 1/1987 | Sauer . |
| 4,641,650 | 2/1987 | Mok . |
| 4,672,969 | 6/1987 | Dew . |
| 4,733,660 | 3/1988 | Itzkan . |

(List continued on next page.)

OTHER PUBLICATIONS

Jain, K. K., "Repair of small blood vessels with the Neodymium-YAG laser: A preliminary report", *Surgery*, 85(6):684–688 (1979).

Vance, C. A. et al., "Laser Assisted Vessel Anastomosis of Coronary Arteries in Vitro: Optimization of Bonding Conditions", *Lasers in Medical Science*, 3:219–227 (1988).

Schober, R. et al., "Laser-Induced Alteration of Collagen Substructure Allows Microsurgical Tissue Welding", *Science*, 232:1421–1422 (1986).

White, R. A., "Technical frontiers for the vascular surgeon: Laser anatomotic welding and angioscopy-assisted intraluminal instrumentation, Symposium: Vascular Applications of Angioscopy and Lasers," *Journal of Vascular Surgery*, 5(4):673–680 (1987).

Chuck, R. S. et al., "Dye-Enhanced Laser Tissue Welding", *Lasers in Surgery and Medicine*, 9:471–477 (1989).

White, R. A., "Argon laser-welded arteriovenous anastomoses", *Journal of Vascular Surgery*, 6(5) 447–453 (1987).

Jain, K. K., "Sutureless Microvacular Anastomosis Using a Neodymium-YAG Laser", *Journal of Microsurgery*, 1:436–439 (1980).

Jain, K. K., *Handbook of Microsurgery*, Charles C. Thomas Co., pp. 37–39 (1983).

(List continued on next page.)

*Primary Examiner*—Stephen C. Pellegrino
*Assistant Examiner*—Mike Peffley
*Attorney, Agent, or Firm*—Jay K. Malkin

[57] ABSTRACT

An effective method for welding corneal and/or scleral tissues. To join the tissues, laser light is applied using a wavelength which enables penetration of the light to a tissue depth of about 0.2–2.0 mm. The wavelength is selected from within one of the following ranges: (1) 1400–1900 nm, or (2) 2100–2400 nm. In epikeratophakia procedures, the wavelength ranges will be 1900–2100 nm or 2400–2650 nm, allowing a tissue penetration depth of about 0.05–0.2 mm. A laser power output value is selected so that the tissue temperature during welding remains at about 44°–60° C. This value is between about 30 mW–1.5 W. The laser light may be applied in the form of a spot-type beam, an elongate beam, or an annular beam. Application of laser light in the foregoing manner enables ocular tissues to be safely and effectively welded, and is useful in corneal transplantation.

24 Claims, 2 Drawing Sheets

U.S. PATENT DOCUMENTS

| | | |
|---|---|---|
| 4,736,745 | 4/1988 | Gluckman . |
| 4,776,335 | 10/1988 | Nakanishi et al. . |
| 4,800,899 | 1/1989 | Elliot . |
| 4,832,004 | 5/1989 | Heckele . |
| 4,848,339 | 7/1989 | Rink et al. . |
| 4,892,098 | 1/1990 | Sauer . |
| 4,917,084 | 4/1990 | Sinofsky . |
| 4,917,486 | 4/1990 | Raven et al. . |
| 4,929,246 | 5/1990 | Sinofsky . |
| 4,950,267 | 8/1990 | Ishihara et al. . |
| 4,968,314 | 11/1990 | Michaels . |
| 4,976,709 | 12/1990 | Sand . |

OTHER PUBLICATIONS

Gailitis, R. P., "Laser Welding of Synthetic Epikeratoplasty Lenticules to the Cornea", *Refractive and Corneal Surgery,* 6:430–436 (1990).

Keates, R. H., "Carbon dioxide laser use in wound sealing and epikeratophakia", *J. Cataract Refract. Surg.,* 13:290–295 (1987).

Curico, J. A. et al., "The Near Infrared Absorption Spectrum of Liquid Water," *Journal of the Optical Society of America,* 41(5):302–304 (1951).

Haufman, H. E. et al., *The Cornea,* pp. 823–847, Churchill Livingstone, New York (1988).

METHOD FOR THE JOINING OF OCULAR TISSUES USING LASER LIGHT

BACKGROUND OF THE INVENTION

The present invention generally relates to the joining of ocular tissues, and more particularly to the welding of ocular tissues (e.g. scleral and corneal tissues) to each other using laser light in a manner which avoids disfigurement and/or destruction of the tissues.

In recent years, many advances have been made in the medical use of laser technology. Techniques involving the application of laser light have proven to be beneficial in many medical fields ranging from cardiology to ophthalmology. For example, substantial developments have been made using laser energy for the welding of blood vessels, arteries, and the like. The laser welding of vascular tissues is discussed in Jain, K. K. et al., "Repair of small blood vessels with the Neodymium-YAG laser: A preliminary report", *Surgery*, 85(6):684–688 (1979). This article provides a general discussion of laser surgical techniques and the advantages thereof. Other articles which discuss the laser welding of vascular tissues include Vance, C. A. et al., "Laser Assisted Vessel Anastomosis of Coronary Arteries in Vitro: Optimization of Bonding Conditions", *Lasers in Medical Science*, 3:219–227 (1988); Schober, R., et al., "Laser-Induced Alteration of Collagen Substructure Allows Microsurgical Tissue Welding", *Science*, 232:1421–1422 (1986); White. R. A., "Technical frontiers for the vascular surgeon: Laser anastomotic welding and angioscopy-assisted intraluminal instrumentation", Symposium: Vascular Applications of Angioscopy and Lasers, *Journal of Vascular Surgery*, 5(4):673–680 (1987); Chuck, R. S., et al., "Dye-Enhanced Laser Tissue Welding", *Lasers in Surgery and Medicine*, 9:471–477 (1989); White, R. A., "Argon laser-welded arteriovenous anastomoses", *Journal of Vascular Surgery*, 6(5) 447–453 (1987); and Jain, K. K., "Sutureless Microvascular Anastomosis Using a Neodymium-YAG Laser", *Journal of Microsurgery*, 1:436–439 (1980). All of the foregoing articles discuss vascular welding experiments involving the use of carbon dioxide lasers (wavelength=10,600 nm), argon lasers (wavelength=488 and 514 nm), or Nd:YAG lasers (wavelength=1064 and 1319 nm).

A number of U.S. Patents also exist which involve the sealing/welding of vascular and other tissues using laser energy. These patents include U.S. Pat. No. 4,917,084 to Sinofsky (laser repair of artery walls and the removal of atherosclerotic plaque using laser energy having a wavelength of 1400–2200 nm); U.S. Pat. No. 4,929,246 to Sinofsky (laser welding of arteries using a laser wavelength of 1400–2500 nm); U.S. Pat. No. 4,892,098 to Sauer (laser welding of vascular tissues using Nd:YAG green laser light [wavelength=510 nm]); U.S. Pat. No. 4,633,870 to Sauer (laser welding of tubular tissues using Nd:YAG and/or carbon dioxide laser light); and U.S. Pat. No. 4,672,969 to Dew (wound closure in the following tissues: skin, nerve fiber, vascular tissues, reproductive tissue structures such as vas deferens or fallopian tubes, gastrointestinal tract, eye tissues, and tendons using a monochromatic beam of laser energy having a wavelength of between 1200–1400 nm). Additional information regarding vascular welding using laser technology is further disclosed in Jain, K. K., *Handbook of Microsurgery*, Charles C. Thomas Co., pp. 37–39 (1983).

Other uses of laser technology are disclosed in U.S. Pat. No. 4,733,660 to Itzkan and U.S. Pat. No. 4,832,004 to Heckele. U.S. Pat. No. 4,733,660 involves the use of laser energy (wavelength=less than 600 nm) for dermatological purposes (e.g. the treatment of hemangioma which is more commonly known as "port wine stain syndrome"). U.S. Pat. No. 4,832,004 discloses a laser laryngoscope which is used in the endoscopic laser treatment of larynx diseases. A wide variety of laser-related medical techniques/equipment are also disclosed in U.S. Pat. No. 4,641,650 to Mok; U.S. Pat. No. 4,736,745 to Gluckman; U.S. Pat. No. 4,800,899 to Eliott; U.S. Pat. No. 4,840,939 to Leveen et al.; U.S. Pat. No. 4,848,339 to Rink et al.; U.S. Pat. No. 4,869,247 to Howard III, et al.; U.S. Pat. No. 4,950,267 to Ishihara et al.; U.S. Pat. No. 4,968,314 to Michaels; and European Patent Specification No. 0327410.

In the area of ophthalmology, a substantial amount of research has been conducted regarding the use of laser light in photocoagulation processes designed to treat a variety of problems, including diabetic retinopathy, retinal tears, glaucoma, and retinal vascular diseases. Various devices designed to implement photocoagulation processes are disclosed in U.S. Pat. No. 3,467,099 to Lotmar; U.S. Pat. No. 3,487,835 to Koester et al.; U.S. Pat. No. 3,547,125 to Tagnon; U.S. Pat. No. 3,930,504 to de Laforcade; U.S. Pat. No. 4,526,170 to Tanner; U.S. Pat. No. 4,537,193 to Tanner; U.S. Pat. No. 4,776,335 to Nakanishi et al.; and U.S. Pat. No. 4,917,486 to Raven et al. These patents disclose the use of a variety of different laser light wavelengths including 418–514 nm (Tanner '193), 800 nm (Raven et al.), and 693 nm (Koester et al.).

Additional research and development in the area of ophthalmology has been reported in a number of other journal articles and patents. For example, U.S. Pat. No. 4,976,709 to Sand discloses the shrinkage of corneal tissues in order to correct vision problems using discrete bursts of laser light having a wavelength of 1800–2550 nm with the applied energy per burst being about 0.01–5.0 joules. Gailitis, R. P., "Laser Welding of Synthetic Epikeratoplasty Lenticules to the Cornea", *Refractive and Corneal Surgery*, 6:430–436 (1990), and Keates, R. H., "Carbon dioxide laser use in wound sealing and epikeratophakia", *J. Cataract Refract. Surg.*, 13:290–295 (1987) both describe the use of a carbon dioxide laser (wavelength=10,600 nm) for the laser welding of epikeratoplasty lenticules to corneal tissues, with such experiments resulting in detectable tissue damage/shrinkage.

Accordingly, a wide variety of work has been done in the medical field using laser technology. However, a substantial need remains for a method wherein ocular tissues, namely corneal and scleral tissues, may be welded together using laser energy in order to produce a weld which avoids fluid leakage and promotes healing. This is especially important with respect to the cornea which serves as the primary refractive surface for producing visual images in the eye. The human cornea is a tough structure which is transparent and has a central thickness of about 0.54 mm. As described in greater detail below, the cornea forms the anterior boundary of the anterior chamber in the eye which contains the aqueous humor. The aqueous humor consists of a clear, watery fluid that is maintained at a pressure of about 15–22 mm Hg. Leakage of the aqueous humor occurs with any perforation of the cornea. Leakage can also occur after the closure of an incision, such as the circular incision made during a corneal transplant procedure. In addition, corneal wounds which are sutured unevenly or have areas of tissue overlap can cause substantial changes in the curvature of the cornea, thereby producing astigmatism. For example, in cataract surgery, an incision of up to 6.0 mm in length is made in the limbus of the eye which comprises the junction between the cornea and sclera. In this surgical procedure, tissue overlap and/or uneven regions of the incision can occur, again causing astigmatism in a patient. Likewise, in corneal transplant surgery, improper wound healing can cause fluid leakage and optical astigmatism. This is especially true in corneal transplant operations, since the incision is substantial in size, normally involving a round wound having a diameter of about 6-9 mm. Furthermore, if wound healing does not properly occur in a corneal transplant operation, the epithelial tissue of the cornea (described in greater detail below) can grow downwardly along a path between the donor and host tissue, thereby causing a delay in tissue healing.

The sclera is a white structure which is thicker than the cornea (e.g. about 0.6 mm thick) and comprises most of the outer covering of the eye. The junction between the cornea and the sclera is known as the limbus as indicated above. A common operation in the sclera is the formation of a superior incision near the limbus in order to remove the crystalline lens. Since the sclera supports the cornea at the edges, and since the cornea forms a strong lens element to focus light within the eye, any minor change in the support of the cornea by the sclera can cause the cornea to become astigmatic. As a result, this can impart optical astigmatism to the cornea. These problems may be caused by the gaping of an incision which, for example, could occur following cataract surgery. Astigmatic changes can also occur during the process of wound healing as a result of traction exerted by fibroblasts on collagen fibrils during wound healing.

The cornea and sclera are comprised of a stroma primarily consisting of fibrous collagen proteins, surrounded by a matrix comprised of other proteins. However, the cornea and sclera actually consist of about 80% by weight water, the importance of which in regard to laser treatment is described in greater detail below. In contrast, layers of cellular tissue make up no more than about 10% of the thickness of the cornea.

While numerous developments have been made with respect to the joining of other tissues (e.g. vascular tissues), a significant need exists for a laser welding method which enables the joining of ocular tissues (e.g. corneal and scleral tissues) without charring and destructive deformation. The present invention satisfies this need in a unique manner as described in greater detail below.

SUMMARY OF THE INVENTION

It is an object of the present invention to provide a tissue welding method using laser technology.

It is another object of the invention to provide a tissue welding method using laser technology which is especially suitable for the joining of ocular tissues, namely, corneal and scleral tissues.

It is another object of the invention to provide a method for the welding of corneal and scleral tissues using laser energy which avoids the charring and deformation thereof.

It is a further object of the invention to provide a method for the welding of corneal and scleral tissues using laser energy which avoids damaging other eye tissues (e.g. the lens and/or retina) during the application of laser light.

It is a still further object of the invention to provide a method for the welding of corneal and scleral tissues using laser energy which is rapid and produces a tissue weld of substantial structural integrity.

It is an even further object of the invention to provide a method for the welding of corneal and scleral tissues using laser energy which is easily performed by an ophthalmic surgeon using a minimal amount of equipment.

In accordance with the present invention, a unique method is disclosed which enables the welding of corneal and/or scleral tissues together without the destructive tissue deformation which is characteristic of other laser welding techniques. In addition, the method of the present invention is highly versatile in that it enables the welding of corneal tissue to corneal tissue, scleral tissue to scleral tissue, and corneal tissue to scleral tissue. The method of the invention produces ocular tissue welds in a rapid manner which have a high degree of structural integrity. Furthermore, the method of the invention avoids damage to other ocular tissues during welding, including but not limited to the lens and retina.

In order to implement the method of the present invention, a first portion of ocular tissue having a leading edge and a second portion of ocular tissue having a leading edge are initially provided. The first portion of ocular tissue and the second portion of ocular tissue may be entirely separate sections of tissue which are to be welded together using the methods described herein. For example, the first portion of ocular tissue may consist of the remaining section of a patient's cornea after the removal of diseased corneal tissue therefrom. In such a case, the first portion of ocular tissue would have a circular leading edge as described in greater detail below. The second portion of ocular tissue would consist of a donor cornea which would also have a circular leading edge substantially the same size and shape as the circular leading edge in the first portion of ocular (e.g. cornea) tissue. In an alternative embodiment, the first and second portions of ocular tissue may actually be part of a single tissue section, with the first and second portions of ocular tissue being separated from each other by a linear or arcuate incision/wound therebetween. The incision/wound would actually consist of the leading edges of the first and second portions of ocular tissue which would need to be sealed for healing to occur. Thus, the present invention is useful in both ocular tissue transplant procedures, and in the closure of wounds in existing tissues.

In order to effectively join the leading edges of the ocular tissues together, the leading edges thereof are first placed adjacent to and against each other. Thereafter, laser light is applied to both of the leading edges simultaneously so that they may be joined together in a secure manner. However, a number of important parameters must first be considered including but not limited to the laser light wavelength, the desired depth of laser light penetration, the laser power output level, and the spatial intensity distribution on the tissue surface (e.g. the size of the illuminated area). All of these factors must be carefully considered or else a number of problems may result. For example, it is desired that the laser light not penetrate too deeply into the tissues being joined. This is especially true with respect to the joining of corneal tissues, wherein excessive laser penetration may result in damage to the underlying ocular tissues, namely, the lens and retina. In a preferred embodiment it is desired that the majority of the laser light (e.g. $(1-1/e)$ or approximately 63%) be absorbed within a tissue depth range of about 0.2-2.0 mm. In order to accomplish this, the laser light wavelength must be selected very carefully. Laser light having an excessively short wavelength will not be effectively absorbed by the desired tissues, and will penetrate too deeply into the ocular tissues. Laser light having an excessively long wavelength will be primarily absorbed near the surface of the desired tissues and will not penetrate deeply enough to produce a strong tissue weld.

In accordance with the present invention, laser light is applied to the ocular tissues within a wavelength range selected from the group consisting of about 1400-1900 nm and about 2100-2400 nm. These wavelength ranges were selected in a manner described in greater detail below, and enable corneal/scleral tissue welding having a proper degree of laser light penetration. Specifically, laser light having a wavelength of about 1400-1900 nm will penetrate ocular tissues to a depth of about 0.2-2.0 mm, and laser light having a wavelength of about 2100-2400 nm will penetrate to a depth of about 0.2-0.5 mm.

It should also be noted that the present invention may be used to secure lenticules to a patient's eye in an epikeratophakia procedure as described in greater detail below. The preferred laser wavelength ranges for this purpose include about 1900-2100 nm and about 2400-2650 nm.

The laser light may be applied to the leading edges of the ocular tissues in a variety of forms. For example, the laser light may be applied in the form of a spot which is continuously moved along the leading edges of the ocular tissues so that tissue welding may occur. In a preferred embodiment, the spot will have a diameter of about 0.1-0.3 mm and will be moved along the leading edges of the ocular tissues at a rate of about 0.5-2.0 mm/minute. In an alternative embodiment, the laser light may be applied to the leading edges of the ocular tissues in an elongate beam formed using conventional optical systems so that the laser light may strike all portions of the leading edges simultaneously. Finally, in the case of corneal transplants and the like wherein the leading edges of the ocular tissues are substantially circular, the laser light may be applied in the form of an annular, ring-like beam again using optical systems known in the art. The ring of laser light will have a size and shape approximating the dimensions of the circular leading edges described above.

Another important factor to consider is the power output level of the laser light being applied. In a preferred embodiment, the power output level will be sufficient to maintain the temperature of the ocular tissues within a range of about 45°-60° C. during welding. Temperatures substantially below this range will not produce welds having a sufficient degree of structural integrity. Temperatures substantially above this range will cause charring, denaturation, tissue disfigurement, or other detrimental effects, especially when corneal surgery is involved. The precise power output level to be used in a given situation will depend on many factors including but not limited to the wavelength of the laser light being used, the specific type of ocular tissue involved, and other extrinsic factors. In addition, power output requirements will vary, depending on how the laser light is applied. For example, a higher power output level is required when an elongate beam or ring of laser light is used, compared with the application of a single spot of laser light. Basically, the required power output level will be approximately 100-1000% higher when an elongate beam or ring-like beam of laser light is used compared with a single spot.

In general, a power output level within a range of about 30 mW-1.5 W will be sufficient for the applications and embodiments of the invention described herein. For the foregoing wavelength ranges, the following power output for 1400-1900 nm, and about 30 mW-750 mW for 2100-2400 nm.

As noted above, a substantial number of factors are involved in the determination of exactly what power output level is appropriate in a given situation. In view of the numerous variables involved, power output within the foregoing ranges may be precisely determined in a specific situation by controlled tissue experiments. Such experiments basically involve preliminary tissue trials using reference tissue samples. Using a given laser wavelength and method of laser application, power output levels are selectively adjusted during the application of laser light to the reference tissue. During laser light application, the temperature of the tissue is monitored using conventional thermocouple devices and the like. As a result of these experiments, a power output level is selected which enables effective welding of the tissues while maintaining the temperature level thereof at between about 45°-60° C. so that excessive, disfiguring shrinkage and other related problems are avoided. The selected power output level is then applied to actual procedures associated with patients.

The present invention as described herein enables ocular tissues (e.g. corneal and/or scleral tissues) to be rapidly welded in a highly efficient manner without destructive deformation, damage to associated ocular tissues, and other related problems. Accordingly, the present invention represents an advance in the art of ocular tissue treatment, as described in greater detail below. These and other objects, features, and advantages of the present invention will be described below in the following Brief Description of the Drawings and Detailed Description of Preferred Embodiments.

DETAILED DESCRIPTION OF PREFERRED EMBODIMENTS

The present invention involves a unique, non-destructive method for effectively joining ocular tissues together using laser energy. The method of the invention avoids destructive tissue deformation and other comparable problems while producing strong and secure welds which are especially important in a variety of ophthalmological applications, including but not limited to corneal transplants.

Figure 1:
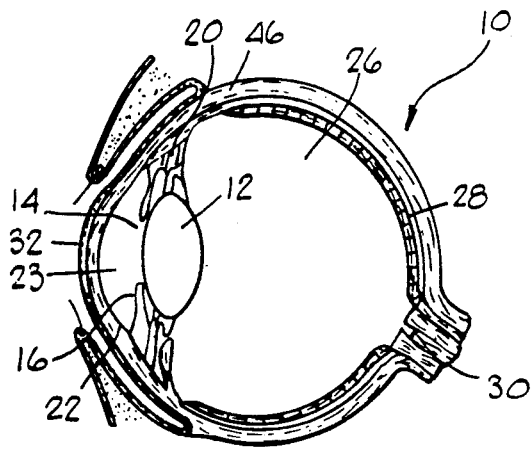
FIG. 1 is an enlarged, cross-sectional, partial view of a human eye showing the various components thereof.

By way of background, FIG. 1 schematically illustrates in cross section a human eye and the components thereof. With reference to FIG. 1, a human eye 10 is illustrated which includes a transparent, crystalline lens 12, with access thereto being provided through an opening or pupil 14, the size of which is controlled using the iris 16. In order to properly focus on objects, the curvature of the lens 12 may be changed through the action of tiny ciliary muscles 20. Directly ahead of the lens 12 and iris 16 is a structure known a the anterior chamber 22 which is filled with a fluid known as the aqueous humor 23. Behind the lens 12 is a region of gel-like fluid known as the vitreous humor 26. Light images passing through the lens 12 and vitreous humor 26 ultimately strike a region of light-sensitive cells known as the retina 28. Stimuli generated by the cells of the retina 28 are ultimately transferred to the brain for interpretation via the optic nerve 30.

Figure 2:
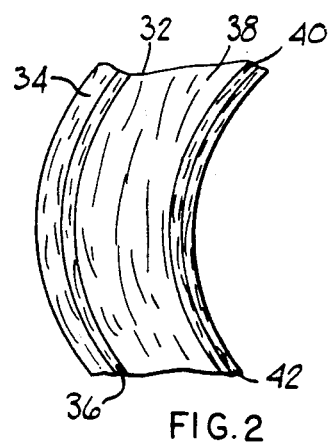
FIG. 2 is an enlarged, cross-sectional view of a portion of corneal tissue showing the various components thereof.

The frontal, exterior portion of the eye 10 is comprised of a transparent zone known as the cornea 32. With reference to FIGS. 1 and 2, the cornea 32 basically includes an outer epithelial layer 34 having an inner layer known as Bowman's membrane 36 adjacent thereto (FIG. 2). Adjacent to the Bowman's membrane 36 is a stromal tissue layer 38 which comprises most of the thickness of the cornea 32. The stromal tissue layer 38 consists mostly of water and collagen. Following the stromal tissue layer 38 as shown in FIG. 2 is a thin layer of tissue known as Descemet's membrane 40 and a final endothelial layer 42.

The cornea 32 is a highly specialized structure that is subject to a wide variety of dystrophies and degenerative diseases which may necessitate corneal replacement. Such diseases typically include keratoconus, keratoglobus, Fuch's dystrophy, interstitial keratitis, scarring due to infection, scarring due to injury, and failed prior transplants. In addition, corneal tissue is highly sensitive to temperature. High temperature levels (e.g. temperatures above about 60° C.) may cause extensive, disfiguring shrinkage and/or physical distortion of the cornea, thereby diminishing the visual acuity of the entire eye structure. Corneal shrinkage is described in U.S. Pat. No. 4,976,709 to Sand as indicated above. The Sand patent involves the application of laser light to intact corneal tissues under conditions which cause intentional, substantial shrinkage of the cornea in order to correct vision defects. However, in corneal transplant procedures and the like, any substantial shrinkage of the corneal tissues may adversely affect a patient's vision and is highly undesirable.

With continued reference to FIG. 1, the cornea 32 is surrounded by a white-colored region of collagenous tissue known as the sclera 46. The sclera 46 is also sensitive to heat in substantially the same manner as the cornea 32.

The goal of the present invention is to provide a method for the welding together of corneal and/or scleral tissues using laser energy in a highly efficient and non-destructive manner. The invention is specifically designed to weld corneal tissue to corneal tissue, scleral tissue to scleral tissue, and corneal tissue to scleral tissue. For the sake of clarity, the method of the present invention shall primarily be discussed with reference to the welding of corneal tissues together since the invention is highly useful in corneal transplant procedures. However, it should be noted that the information provided herein shall also be equally applicable to the welding of scleral tissue to scleral tissue and corneal tissue to scleral tissue except where otherwise indicated.

In order to effectively weld the foregoing tissue together using laser light, the application thereof must be very precisely controlled so that the possibility of tissue charring, extensive disfiguring shrinkage (e.g. deformation), or other damage is minimized. More specifically, the laser light wavelength must be carefully selected in order to: (1) control laser penetration depth so that underlying tissue damage is prevented; (2) impart most of the laser energy to the desired tissue; and (3) control the scattering of laser light by the tissue being treated. In addition, the laser power output level must be precisely controlled so that excessive tissue heating/destructive disfiguration does not occur.

By way of background, there are two basic types of tissue welding which may be accomplished using laser technology. The first method involves the heating of protein materials to form a coagulum (e.g. a mass of protein in a denatured state). The second method involves the gentle stimulation of tissue molecules through the action of laser energy and/or heat until they become adhesive and form new molecular bonds by recombination of charged groups associated therewith. Thereafter, the affected tissue undergoes fibroblastic invasion, new collagen synthesis, and the removal of damaged tissue. This ultimately results in the desired state of repair. The present invention involves the controlled use of laser energy to accomplish tissue welding using the second method described above which is ideally suited for the repair/healing of ocular tissues in a non-destructive manner.

To effectively weld ocular tissues using laser energy, the proper laser light wavelength must first be selected. With respect to corneal and scleral tissues, a laser wavelength must be selected which penetrates sufficiently to ensure that an adequate weld is formed. However, a wavelength must also be selected which does not allow the laser energy to penetrate too deeply into the tissues being treated. Excessive laser penetration can cause significant damage to underlying tissue structures including but not limited to the lens and/or retina.

It is desirable and preferred that an infrared laser wavelength be used which has a water absorption coefficient of between about 10/cm–50/cm. These values inversely correspond to a water penetration depth of about 0.2–2.0 mm. It is customary to express the penetration of infrared laser light into ocular tissues (e.g. corneal and scleral tissues) with reference to the absorption/penetration depth of laser light in water. This is true because these tissues are approximately 80% water, with the properties thereof being similar to those of water relative to laser light absorption/penetration. Further information regarding the absorption of infrared laser light into water is described in Curcio, J. A., "The Near Infrared Absorption Spectrum of Liquid Water", *Journal of the Optical Society of America*, 41(5):302–304 (1951) which is incorporated herein by reference.

Figure 6:
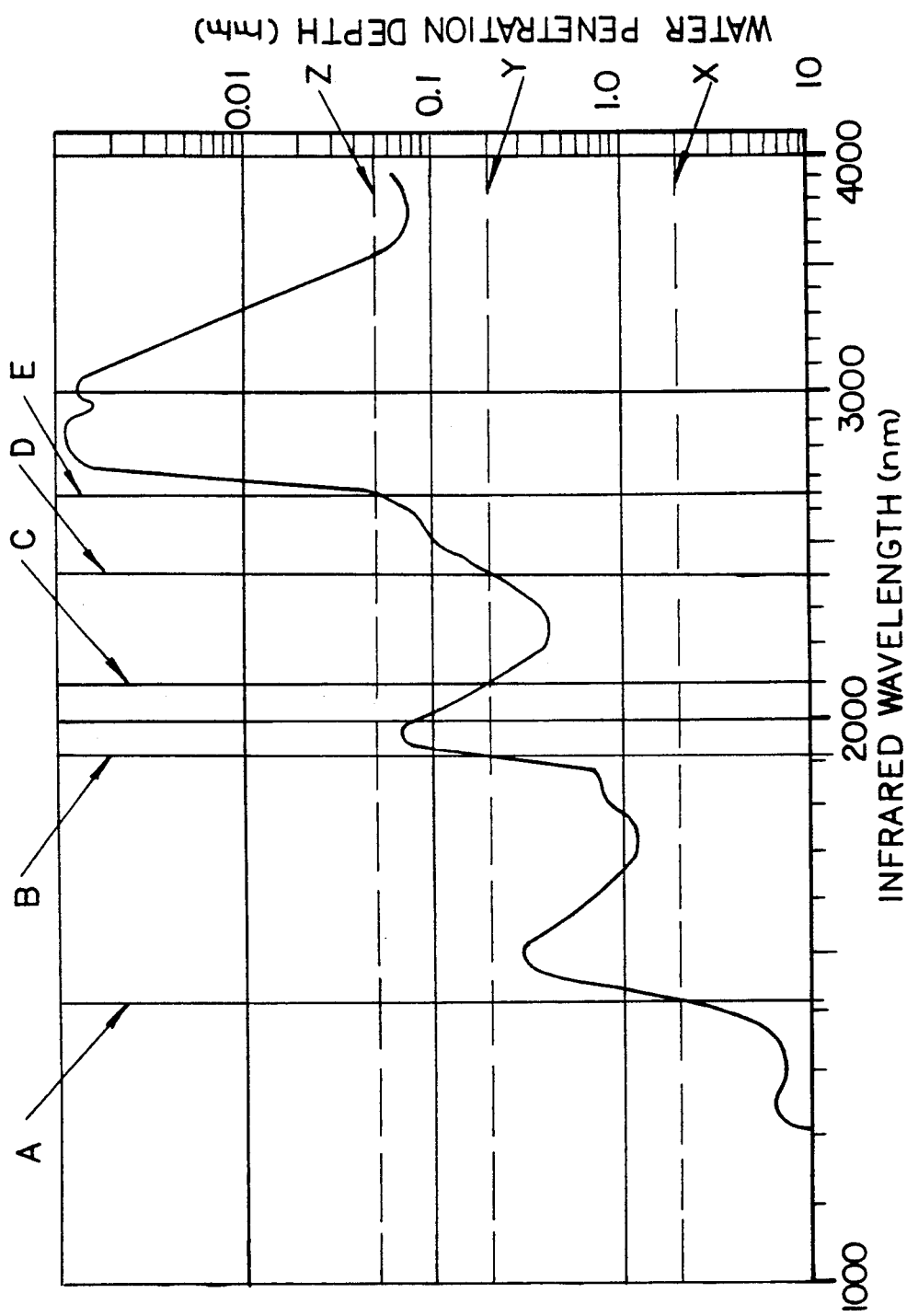
FIG. 6 is a graphic representation of laser light penetration depth in water v. infrared laser light wavelength.

FIG. 6 provides a graphic representation of laser light penetration (e.g. absorption depth for 63% $(1-1/e)$) in water v. infrared laser light wavelength. In the graph of FIG. 6, the dashed horizontal lines "X" and "Y" correspond to a water penetration depth of between about 0.2–2.0 mm. As noted above, a direct correlation between water penetration depth and penetration depth in ocular tissue (e.g. corneal/scleral tissues) can be made since corneal/scleral tissues are mostly water. The infrared laser light wavelengths along the curve in FIG. 6 which fall between the horizontal dashed lines "X" and "Y" represent the wavelength ranges which will provide an ocular tissue penetration depth of between about 0.2–2.0 mm. As noted above, this depth is highly suitable for tissue welding in accordance with the present invention. The laser wavelengths between horizontal dashed lines "X" and "Y" fall into two ranges as follows: (1) about 1400–1900 nm, and (2) about 2100–2400 nm. With continued reference to FIG. 6, wavelength range (1) is between vertical lines "A" and "B", and wavelength range (2) is between vertical lines "C" and "D". A laser system tuned to an appropriate wavelength within one of these ranges will penetrate to a depth of approximately 0.2–2.0 mm in water, and to a similar depth in tissues composed primarily of water (e.g. corneal and/or scleral tissues). Specifically, in accordance with FIG. 6, laser light having a wavelength of about 1400–1900 nm will penetrate ocular tissues to a depth of about 0.2–2.0 mm, and laser light having a wavelength of about 2100–2400 nm will penetrate to a depth of about 0.2–0.5 mm.

Of the total energy involved, $(1-1/e)$ or approximately 63% thereof will be absorbed within the tissue depth range described above (e.g. between about 0.2–2.0 mm). A tunable laser system known in the art as described below can be used to effectively provide the desired wavelength so that a specific, optimum tissue penetration depth can be achieved.

In direct contrast, infrared laser light having a wavelength along each portion of the curve in FIG. 6 which falls above dashed line "Y" will have an insufficient penetration depth to effectively weld the full thickness of corneal and/or scleral tissues. For example, conventional carbon dioxide laser systems producing laser light having a wavelength of about 10,600 nm will typically result in welds which fail to have a sufficient degree of structural integrity. Laser light having a wavelength along each portion of the curve in FIG. 6 which falls below dashed line "X" will have a corresponding penetration depth which is sufficiently great to damage ocular structures behind the cornea/sclera including but not limited to the lens and/or retina. Conventional argon laser systems which produce laser light having a wavelength of about 488 and 514 nm and Nd:YAG laser light having wavelengths of about 1064 and 1319 nm will have too high a degree of tissue penetration, and are therefore undesirable for the purposes set forth herein.

The production of laser light within the above-described ranges may be accomplished using a wide variety of conventional laser systems. A list of exemplary laser systems known in the art which are suitable for use in accordance with the present invention includes the following: (1) HF R-branch chemical laser (producing wavelengths of 2300–2500 nm corresponding to water penetration depths of 0.2–0.5 mm); (2) Tm:YAG 1950–2150 nm laser; (3) Ho:YAG 2100 nm laser; (4) Co-MgFz 1750–2500 nm laser; (5) Nd:YAG 1414 and 1444 nm laser; (6) Diode 1520–1580 nm laser; (7) Diode 1550 nm laser; (8) Diode 1480 nm laser; (9) Diode 1100–1600 nm tunable laser; (10) Xenon-Helium 2000–4000 nm tunable laser; (11) Raman-shifted Nd:YAG 1540 nm laser; and (12) F-center 1450–1750 nm laser. However, it should be noted that the present invention shall not be limited to the above-described laser systems. Other systems known in the art which are suitable for the purposes described herein may also be used.

Another factor to be considered is the power output level of the laser energy being applied. The precise power output level must be controlled so that a secure weld may be produced without excess heating and the charring/deformation caused thereby. The power output level will vary, depending on the laser wavelength being used and the desired tissue penetration depth. For the purposes specified herein, a broad power output range of about 30 mW–1.5 W is appropriate. For each particular wavelength range specified herein, the following power output sub-ranges are appropriate and preferred as listed in Table I below:

TABLE I

| LASER WAVELENGTH RANGE (nm) | POWER OUTPUT RANGE |
|---|---|
| 1400–1900 | 60 mW–1.5 W |
| 2100–2400 | 30 mW–750 mW |

In addition, it should be noted that the exact power output level will depend on the thickness of the ocular tissue being welded. Also, the power output level will depend on the type of beam used to accomplish welding. Examples of different beam types will be described below, and include but are not limited to a spot-type beam, an elongate beam, and/or an annular, ring-like beam. Larger beam configurations (e.g. annular beams) will require greater power output levels such as those near the upper limits of the ranges listed in Table I. Specifically, laser light delivered in the form of elongate or ring-like beams will require a power output level which is approximately 100–1000% greater than the power output level used when spot-type beams are involved. Thus, within the power output ranges listed in Table I, a variety of factors must be considered. However, as a general guideline, a power output level should be selected so that the ocular tissues are heated to and within a temperature range of about 45°–60° C. during laser light application. The heating of ocular tissues within this range enables tissue welding to occur while substantially avoiding the destructive deformation thereof. In order to select an exact power output level within the foregoing ranges, controlled tissue experiments are preferably undertaken. Such experiments basically involve preliminary tissue trials with reference tissue samples. Using a selected laser light wavelength and method of laser application, the power output levels are selectively adjusted during application of the laser light to the reference tissue. During laser application, the temperature of the reference tissue is monitored using conventional thermocouple devices and the like. As a result, a power output level is selectively determined which enables effective welding of the tissues while maintaining the temperature level thereof at between about 45°-60° C. so that destructive shrinkage (e.g. deformation) and other related problems are avoided. This power output level is then used in actual procedures associated with patients. In addition, it may be desirable to use a slightly higher power level for a short interval in order to raise the tissue temperature as desired for welding, then reduce the power to a level sufficient to maintain tissue temperature for a period sufficient to ensure welding.

Finally, as indicated above, there are a number of methods which may be used to apply the laser light to actual tissue materials. These methods are described in the following Examples:

EXAMPLE 1

Figure 3:
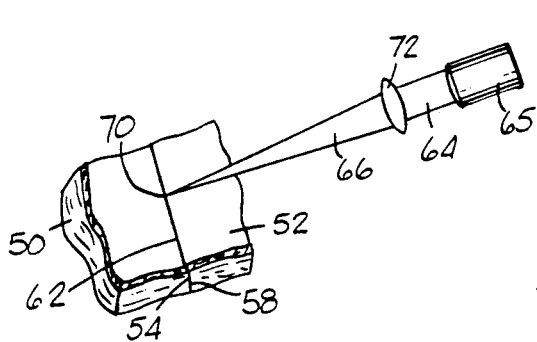
FIG. 3 is a schematic illustration of the welding of ocular tissues in accordance with the present invention using laser light applied in the form of a single spot.

This method is schematically illustrated in FIG. 3. Basically, a first portion 50 of ocular material and a second portion 52 of ocular material are provided. The first portion 50 may consist of scleral tissue or corneal tissue. Likewise, the second portion 52 may also consist of either scleral tissue or corneal tissue. As noted above, the present invention may be used to weld corneal tissue to corneal tissue, scleral tissue to scleral tissue, or scleral tissue to corneal tissue. In addition, the first portion 50 and second portion 52 of ocular tissue may come from the same source (e.g. a human cornea divided into the first portion 50 and second portion 52 by an incision/tear therein), or may come from different sources (e.g. as would be the case in corneal transplant procedures).

With continued reference to FIG. 3, the first portion 50 has a leading edge 54 and the second portion 52 has a leading edge 58. While the leading edges 54, 58 shown in FIG. 3 are substantially linear, they may also be arcuate or circular, as will be described in greater detail below.

In order to weld the leading edges 54, 58 together in accordance with the present invention, the leading edges 54, 58 are first placed directly adjacent to and against each other so that a juncture or seam 62 is produced which has no gaps, uneven portions, and the like. Thereafter, laser light 64 having a wavelength of 2350 nm (giving a tissue penetration depth of about 0.35 mm) and a power output level of 65 mW, is applied from a source 65 (an HF R-branch chemical laser) in the form of a beam 66. The beam 66 is configured so that the laser light 64 contacts both of the leading edges 54, 58 simultaneously at the seam 62 in the form of a single spot 70 (FIG. 3). In a preferred embodiment, the spot 70 has a diameter of about 0.1–0.3 mm which is produced using a conventional optical adjustment system 72 which basically consists of a condensing lens and limiting apertures well-known in the art. The spot 70 is then moved continuously along the leading edges 54, 58 at the seam 62 in order to effectively weld them together. Using this technique, it takes about 30–120 seconds for tissue joining to occur. Thus, it is preferred that the spot 70 be moved continuously along the leading edges 54, 58 at a rate of about 0.5–2.0 mm/minute. The resulting tissue weld is clean, secure, and has no gaps or uneven portions thereof. It should also be noted that in this Example and in the other Examples provided below, the laser light wavelengths, power output levels and the like may be varied within the broad ranges defined above.

EXAMPLE 2

Figure 4:
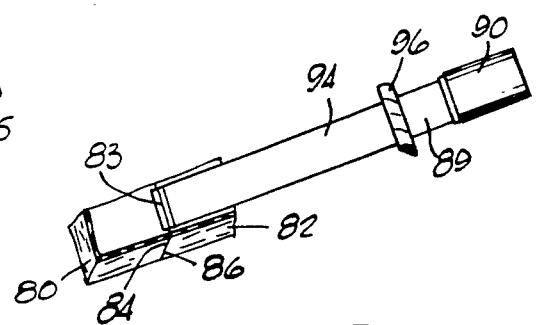
FIG. 4 is a schematic illustration of the welding of ocular tissues in accordance with the present invention using laser light applied in the form of an elongate beam.

First and second portions 80, 82 of ocular tissue are provided which are separated by an incision 83. The incision 83 has leading edges 84, 86. The first and second portions 80, 82 of ocular tissue in this method are of the same type and character as the first and second portions 50, 52 of ocular tissue discussed in example 1. In this example (as shown in FIG. 4), the leading edges 84, 86 are substantially linear, but again could be arcuate or circular. The leading edges 84, 86 are then positioned adjacent to and against each other in the same manner described above relative to the leading edges 54, 58 in example 1 so that the incision 83 has no gaps, uneven portions, and the like. In this example, the incision 83 has a length of about 5 mm. Laser light 89 having a wavelength of 2350 nm (giving a penetration depth of about 0.35 mm) and a power output level of approximately 200 mW is then applied from a source 90 (an HF R-branch chemical laser) to the leading edges 84, 86 simultaneously at the incision 83 in the form of an elongate beam 94. The beam 94 has a length and width sufficient to enable all portions of the leading edges 84, 86 to be simultaneously illuminated (FIG. 4). The beam 94 in this method (and in other methods involving elongate beams) is preferably applied for a time period of about 30–120 seconds. This procedure is much more rapid than that disclosed in method 1. The production of elongate beam 94 would involve the use of an optical adjustment system 96 which is well known in the art. Such a system would typically involve a cylindrical focusing lens, which focuses light along one axis but not the other, thereby producing a beam of dimensions appropriate to illuminate all portions of the leading edges as described. Alternately, a rotating or vibrating mirror may be used to mechanically sweep a beam as described in example 1 so as to rapidly illuminate all portions of the leading edges. Both of these systems are known in the art and use conventional components.

It should also be noted that the power output level might need to be moderately increased if the incision 83 is longer.

EXAMPLE 3

Figure 5:
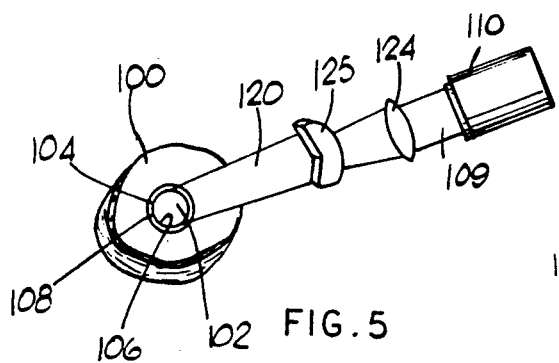
FIG. 5 is a schematic illustration of the welding of ocular tissues in accordance with the present invention during a corneal transplant procedure using laser light applied in the form of an annular, ring-like beam.

This example again involves first and second portions 100, 102 of ocular tissue with leading edges 104, 106. The first and second portions 100, 102 of ocular tissue described in this example both consist of corneal tissues. In this example (as shown in FIG. 5), the leading edges 104, 106 are substantially circular as illustrated. The circular leading edges 104, 106 of this method are comparable to those encountered in a corneal transplant procedure. If a corneal transplant procedure was actually involved, the first portion 100 of ocular tissue would consist of corneal tissue from one source (e.g. a patient), while the second portion 102 of ocular tissue Would consist of corneal tissue from a second source (e.g. from a human donor, or from artificial corneal tissue materials known in the art). The first and second portions 100, 102 would then be placed directly adjacent to and against each other so that no gaps, uneven regions, or the like are evident in order to produce a circular juncture or seam 108. Thereafter, laser light 109 having a wavelength of 2350 nm (giving a tissue penetration depth of about 0.35 mm) and a power output level of 650 mW is applied from a source 110 (an HF R-branch chemical laser) onto the leading edges 104, 106 simultaneously at the seam 108 in the form of an annular, ring-like beam 120 so that all portions of the leading edges 104, 106 are exposed to laser light simultaneously (FIG. 5). The ring-like beam 120 as described herein could be adjustable to different diameters in order to coincide with the incision of a trephine used in penetrating keratoplasty. Such a ring-like beam 120 could be produced using an optical adjustment system known in the art comprised of conventional optical components including but not limited to a condensing lens 124, beam rotating mirror assemblies (not shown), rotating angled optical wedges (not shown), and/or an axicon 125. In this example (and in other examples involving the application of an annular, ring-like beam), the beam 120 is preferably applied for a time period of about 30–120 seconds.

It should be noted that the present invention shall not be limited exclusively to the methods and practices described above which are provided for example purposes only. Other procedures may be used in accordance with the invention to accomplish the goals set forth herein. In addition, the foregoing laser application methods of the present invention may be used either alone or in combination with traditional physical tissue joining systems (e.g. sutures or other mechanical devices). Tests have shown that the reliability of many tissue junctions when held by a combination of laser welds and sutures is found to be greater than that for either welds or sutures alone. The sutures impart good alignment/apposition of tissue, and provide mechanical strength, while the laser welds provide complete absence of fluid leakage, and stimulate rapid wound healing.

Table II below provides exemplary laser light wavelength and power output levels which may be used to effectively weld corneal and/or scleral tissues in accordance with the present invention:

TABLE II

| WAVE LENGTH (nm) | POWER | PENETRATION DEPTH (mm) | BEAM TYPE |
|---|---|---|---|
| 1480–1550 | 90 mW | 0.25 | 0.2 mm dia. spot |
| 1480–1550 | 450 mW | 0.25 | 6 mm dia. ring |
| 2100 | 64 mW | 0.2 | 0.2 mm dia spot |
| 2100 | 320 mW | 0.2 | 6 mm dia. ring |
| 2364 | 75 mW | 0.3 | 0.2 mm dia spot |
| 2364 | 375 mW | 0.3 | 6 mm dia. ring |

It should be noted that the information provided in Table II is for example purposes only, and the present invention shall not be limited to the specific values listed therein. Other wavelength and power output levels may be used in accordance with the wavelength/power output ranges presented above.

In addition, it should also be noted that the present invention is applicable to a procedure known as "epikeratophakia". Epikeratophakia is a procedure which involves the attachment of a "lenticule" onto a patient's existing cornea so that visual correction is achieved more permanently compared with the use of a removable contact lens.

Figure 7:
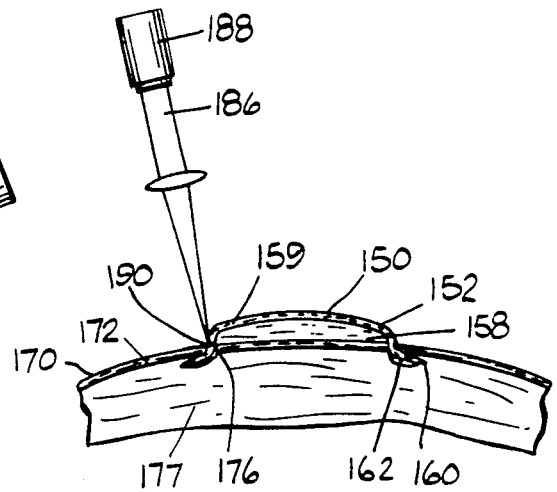
FIG. 7 is a schematic illustration of the use of laser light in accordance with the present invention in an epikeratoplasty procedure.

With reference to FIG. 7, a lenticule 150 (shown schematically in cross section) is illustrated which consists of a substantially round, convex portion 152 of human or animal donor corneal tissue. In addition, research has been conducted regarding the use of synthetic lenticules. Exemplary materials used to produce synthetic lenticules include but are not limited to reconstituted collagen, hydrogels, and chemically stabilized gelatins. When lenticules made from live corneal tissue materials are used, the epithelium is removed and the rear side of the live tissue is lathed in order to remove the endothelial layer, Descemet's layer, and a portion of the stromal tissue layer therefrom (see FIG. 2) so that the Bowman's layer (reference number 36 in FIG. 2 and reference number 159 in FIG. 7) may be exposed. Thus, the lenticule 150 of FIG. 7 consists mostly of the Bowman's layer 159 and a portion of the stromal layer 158. Thereafter, the outer edge 160 of the lenticule 150 is formed into an outwardly extending annular skirt 162 as illustrated schematically in cross section in FIG. 7. The skirt 162 is formed by lathing the edge of the lenticule as thin as possible, allowing sufficient strength for handling and leaving Bowman's layer 159 intact. All of these procedures (and epikeratophakia in general) are conventional and known in the art as described in Kaufman, H. E. et al., The Cornea, pp. 823–847 (Ch. 32), Churchill Livingstone, New York (1988), which is incorporated herein by reference.

The patient's cornea 170 as shown in FIG. 7 is then abraded using an abrasive device known in the art to expose the Bowman's layer 172. A round-bladed instrument known as a trephine is then used to cut a round incision into the stroma 177 of the cornea 170. A blunt spatulate instrument (not shown) is thereafter used to form an open region 176 in the stroma 177. The open region 176 is sized to receive the skirt 162 of the lenticule 150 as illustrated in FIG. 7. Again, the foregoing procedures are conventional and known in the art.

In order to permanently secure the lenticule 150 to the cornea 170 in the configuration shown in FIG. 7, a previously known method involved the use of conventional sutures and the like. However, in accordance with the present invention, laser light having a wavelength within one of the following ranges may be used to weld the lenticule 150 and cornea 170 together: about 1900–2100 nm and about 2400–2650 nm (corresponding to a water penetration depth of about 0.05–0.2 mm which is represented by dashed lines "Z" and "Y" in FIG. 6). With continued reference to FIG. 6, the foregoing wavelength ranges are shown along the curve of FIG. 6 between vertical lines "B" and "C" (about 1900–2100 nm) and between vertical lines "D" and "E" (about 2400–2650 nm). The preferred power output level for this procedure would be about 15 mW–750 mW. The laser application technique described above in method 1 using a spot-type beam may be employed (e.g. involving laser light having an exemplary wavelength of 2579 nm, with a power output of 30 mW, spot size of 0.2 mm in diameter, and spot movement rate of 0.5–2.0 mm/minute.)

As shown schematically in FIG. 7, laser light 186 may be applied from a conventional source 188 (selected from the list of laser units described above) to the juncture 190 where the lenticule 150 contacts the cornea 170 (previously prepared as described above). Using this technique, the laser light 186 contacts both cornea 170 and lenticule 150 simultaneously so that they may be joined together. Welding in this manner joins the Bowman's layer 159 of the lenticule 150 directly to the Bowman's layer 172 of the cornea 170.

As indicated herein, the present invention represents an advance in the art of ocular tissue welding. The invention enables delicate ocular tissues (e.g. corneal and/or scleral tissues) to be welded without charring, destructive deformation, or other comparable problems, and is widely useful in a number of important medical procedures. Having herein described preferred embodiments of the present invention, it is anticipated that suitable modifications may be made thereto which remain within the scope of the invention. For example, the specific types of laser units to be used in accordance with the invention may be varied, as well as the optical delivery systems and hardware associated therewith. Thus, the present invention shall only be construed in accordance with the following claims:

The invention that is claimed is:

1. A method for the welding of ocular tissues to each other, said method comprising the steps of:

provided a first portion of ocular tissue selected from the group consisting of corneal tissue and scleral tissue, and a second portion of ocular tissue selected from the group consisting of corneal tissue and scleral tissue, said first portion of ocular tissue having a leading edge and said second portion of ocular tissue having a leading edge;

positioning said leading edge of said first portion of ocular tissue directly adjacent to and against said leading edge of said second portion of ocular tissue; and applying infrared laser light from a source thereof to both said leading edge of said first portion of ocular tissue and said leading edge of said second portion of ocular tissue simultaneously, said laser light having a wavelength sufficient to enable said laser light to penetrate said first portion of ocular tissue and said second portion of ocular tissue to a depth of about 0.2-2.0 mm so that said leading edge of said first portion of ocular tissue may be securely welded to said leading edge of said second portion of ocular tissue, said wavelength being within a wavelength range selected from the group consisting of about 1400-1900 nm and about 2100-2400 nm, said laser light having a power output level sufficient to maintain said first portion of ocular tissue and said second portion of ocular tissue at a temperature of about 45°-60° C. during said applying of said laser light.

2. The method of claim 1 wherein said first portion of ocular tissue is comprised of corneal tissue and said second portion of ocular tissue is comprised of corneal tissue.

3. The method of claim 1 wherein said first portion of ocular tissue is comprised of corneal tissue and said second portion of ocular tissue is comprised of scleral tissue.

4. The method of claim 1 wherein said first portion of ocular tissue is comprised of scleral tissue and said second portion of ocular tissue is comprised of scleral tissue.

5. The method of claim 1 wherein said power output level is about 30 mW-1.5 W.

6. The method of claim 1 wherein said applying of said laser light comprises the step of delivering said laser light to said leading edge of said first portion of ocular tissue and to said leading edge of said second portion of ocular tissue in the form of a spot which is moved continuously along said leading edge of said first portion of ocular tissue and said leading edge of said second portion of ocular tissue in order to securely weld said first portion of ocular tissue and said second portion of ocular tissue together.

7. The method of claim 1 wherein said applying of said laser light comprises the step of delivering said laser light to said leading edge of said first portion of ocular tissue and to said leading edge of said second portion of ocular tissue in the form of an elongate beam having a size and shape sufficient to strike all of said leading edge of said first portion of ocular tissue and all of said leading edge of said second portion of ocular tissue simultaneously.

8. The method of claim 1 wherein said leading edge of said first portion of ocular tissue and said leading edge of said second portion of ocular tissue are both circular in configuration, and said applying of said laser light comprises the step of delivering said laser light to said leading edge of said first portion of ocular tissue and to said leading edge of said second portion of ocular tissue in the form of a circular beam having a size and shape sufficient to strike all of said leading edge of said first portion of ocular tissue and all of said leading edge of said second portion of ocular tissue simultaneously.

9. A method for the welding of ocular tissues to each other comprising the steps of:

providing a first portion of ocular tissue selected from the group consisting of corneal tissue and scleral tissue, and a second portion of ocular tissue selected from the group consisting of corneal tissue and scleral tissue, said first portion of ocular tissue having a leading edge and said second portion of ocular tissue having a leading edge;

positioning said leading edge of said first portion of ocular tissue directly adjacent to and against said leading edge of said second portion of ocular tissue; and applying infrared laser light from a source thereof to both said leading edge of said first portion of ocular tissue and said leading edge of said second portion of ocular tissue simultaneously, said laser light having a wavelength sufficient to enable said laser light to penetrate said first portion of ocular tissue and said second portion of ocular tissue to a depth of about 0.2-2.0 mm in order to securely weld said leading edge of said first portion of ocular tissue to said leading edge of said second portion of ocular tissue, said wavelength being about 1400-1900 nm, said laser light having a power output level sufficient to maintain said first portion of ocular tissue and said second portion of ocular tissue at a temperature of 45°-60° C. during said applying of said laser light, said power output level being about 60 mW-1.5 W.

10. The method of claim 9 wherein said applying of said laser light comprises the step of delivering said laser light to said leading edge of said first portion of ocular tissue and to said leading edge of said second portion of ocular material in the form of a spot which is moved continuously along said leading edge of said first portion of ocular tissue and said leading edge of said second portion of ocular tissue in order to securely weld said first portion of ocular tissue and said second portion of ocular tissue together.

11. The method of claim 9 wherein said applying of said laser light comprises the step of delivering said laser light to said leading edge of said first portion of ocular tissue and to said leading edge of said second portion of ocular tissue in the form of an elongate beam having a size and shape sufficient to strike all of said leading edge of said first portion of ocular tissue and all of said leading edge of said second portion of ocular tissue simultaneously.

12. The method of claim 9 wherein said leading edge of said first portion of ocular tissue and said leading edge of said second portion of ocular tissue are both circular in configuration, and said applying of said laser light comprises the step of delivering said laser light to said leading edge of said first portion of ocular tissue and to said leading edge of said second portion of ocular tissue in the form of a circular beam having a size and shape sufficient to strike all of said leading edge of said first portion of ocular tissue and all of said leading edge of said second portion of ocular tissue simultaneously.

13. The method of claim 9 wherein said first portion of ocular tissue is comprised of corneal tissue and said second portion of ocular tissue is comprised of corneal tissue.

14. The method of claim 9 wherein said first portion of ocular tissue is comprised of corneal tissue and said second portion of ocular tissue is comprised of scleral tissue.

15. The method of claim 9 wherein said first portion of ocular tissue is comprised of scleral tissue and said second portion of ocular tissue is comprised of scleral tissue.

16. A method for the welding of ocular tissues to each other comprising the steps of:
providing a first portion of ocular tissue selected from the group consisting of corneal tissue and scleral tissue, and a second portion of ocular tissue selected from the group consisting of corneal tissue and scleral tissue, said first portion of ocular tissue having a leading edge and said second portion of ocular tissue having a leading edge;
positioning said leading edge of said first portion of ocular tissue directly adjacent to and against said leading edge of said second portion of ocular tissue; and
applying infrared laser light from a source thereof to both said leading edge of said first portion of ocular tissue and said leading edge of said second portion of ocular tissue simultaneously, said laser light having a wavelength sufficient to enable said laser light to penetrate said first portion of ocular tissue and said second portion of ocular tissue to a depth of about 0.2–0.5 mm in order to securely weld said leading edge of said first portion of ocular tissue to said leading edge of said second portion of ocular tissue, said wavelength being about 2100–2400 nm, said laser light having a power output level sufficient to maintain said first portion of ocular tissue and said second portion of ocular tissue at a temperature of about 45°–60° C. during said applying of said laser light, said power output level being about 30 mW–750 mW.

17. The method of claim 16 wherein said applying of said laser light comprises the step of delivering said laser light to said leading edge of said first portion of ocular tissue and to said leading edge of said second portion of ocular material in the form of a spot which is moved continuously along said leading edge of said first portion of ocular tissue and said leading edge of said second portion of ocular tissue in order to securely weld said first portion of ocular tissue and said second portion of ocular tissue together.

18. The method of claim 16 wherein said applying of said laser light comprises the step of delivering said laser light to said leading edge of said first portion of ocular tissue and to said leading edge of said second portion of ocular tissue in the form of an elongate beam having a size and shape sufficient to strike all of said leading edge of said first portion of ocular tissue and all of said leading edge of said second portion of ocular tissue simultaneously.

19. The method of claim 16 wherein said leading edge of said first portion of ocular tissue and said leading edge of said second portion of ocular tissue are both circular in configuration, and said applying of said laser light comprises the step of delivering said laser light to said leading edge of said first portion of ocular tissue and to said leading edge of said second portion of ocular tissue in the form of a circular beam having a size and shape sufficient to strike all of said leading edge of said first portion of ocular tissue and all of said leading edge of said second portion of ocular tissue simultaneously.

20. The method of claim 16 wherein said first portion of ocular tissue is comprised of corneal tissue and said second portion of ocular tissue is comprised of corneal tissue.

21. The method of claim 16 wherein said first portion of ocular tissue is comprised of corneal tissue and said second portion of ocular tissue is comprised of scleral tissue.

22. The method of claim 16 wherein said first portion of ocular tissue is comprised of scleral tissue and said second portion of ocular tissue is comprised of scleral tissue.

23. A method for the welding of an epikeratoplasty lenticule to corneal tissue comprising the steps of:
providing a portion of corneal tissue;
providing an epikeratoplasty lenticule;
placing said epikeratoplasty lenticule in contact with said corneal tissue; and
applying infrared laser light from a source thereof to said epikeratoplasty lenticule and said corneal tissue simultaneously at a position on said corneal tissue where said epikeratoplasty lenticule comes in contact with said corneal tissue, said laser light having a wavelength within a wavelength range selected from the group consisting of about 1900–2100 nm and about 2400–2650 nm.

24. The method of claim 23 wherein said laser light has a power output level of about 15 mW–750 mW.

* * * * *

UNITED STATES PATENT AND TRADEMARK OFFICE
CERTIFICATE OF CORRECTION

PATENT NO. : 5,290,272
DATED : March 1, 1994
INVENTOR(S) : Burstein, et al

It is certified that error appears in the above-indentified patent and that said Letters Patent is hereby corrected as shown below:

On the Title Page, Item [57], line 11, delete "44" and insert ---45---.
Column 1, line 1, delete "Handbood" and insert ---Handbook---.
Column 6, line 15, between "output" and "for" insert ---levels are appropriate and preferred: about 60 mW - 1.5 W---.
Column 7, line 24, delete "known a" and insert ---known as---.
Column 8, line 17, delete "tissue" and insert ---tissues---.
Column 10, line 5, delete "(4) Co-MgF$_z$" and insert ---(4) Co-MgF$_2$---.
Column 16, line 41, between "of" and "45" insert ---about---.

Signed and Sealed this

Twelfth Day of July, 1994

Attest:

BRUCE LEHMAN

Attesting Officer   Commissioner of Patents and Trademarks